(12) United States Patent
Lee et al.

(10) Patent No.: US 9,886,550 B2
(45) Date of Patent: Feb. 6, 2018

(54) MEDICAL PUMP WITH OPERATOR-AUTHORIZATION AWARENESS

(71) Applicant: Zyno Medical, LLC., Natick, MA (US)

(72) Inventors: Chaoyoung Lee, Weston, MA (US); Todd Sjolander, North Grafton, MA (US); Mei Zhang, Sharon, MA (US)

(73) Assignee: Zyno Medical, LLC, Natick, MA (US)

( * ) Notice: Subject to any disclaimer, the term of this patent is extended or adjusted under 35 U.S.C. 154(b) by 0 days.

(21) Appl. No.: 14/190,312

(22) Filed: Feb. 26, 2014

(65) Prior Publication Data
US 2014/0194817 A1 Jul. 10, 2014

Related U.S. Application Data

(63) Continuation-in-part of application No. 13/489,620, filed on Jun. 6, 2012.
(Continued)

(51) Int. Cl.
*G06F 19/00* (2011.01)
*A61M 5/172* (2006.01)
(Continued)

(52) U.S. Cl.
CPC ..... *G06F 19/3412* (2013.01); *A61M 5/14228* (2013.01); *G06F 19/3418* (2013.01); *G06F 19/3468* (2013.01); *A61M 5/1456* (2013.01); *A61M 2005/14208* (2013.01); *A61M 2205/3553* (2013.01); *A61M 2205/3584* (2013.01); *A61M 2205/3592* (2013.01); *A61M 2205/50* (2013.01); *A61M 2205/502* (2013.01); *A61M 2205/52* (2013.01); *A61M 2205/6009* (2013.01);
(Continued)

(58) Field of Classification Search
CPC ............ G06F 19/3468; G06F 19/3412; G06F 19/3418; G06F 19/3456; G06F 19/3406; G06F 19/326
USPC ......... 604/151, 66, 67, 131, 65, 30, 31, 500, 604/503
See application file for complete search history.

(56) References Cited

U.S. PATENT DOCUMENTS 5,681,285 A * 10/1997 Ford ..................... A61M 5/172
604/151
7,515,060 B2 4/2009 Blomquist
(Continued)

*Primary Examiner* — Kevin C Sirmons
*Assistant Examiner* — William Carpenter
(74) *Attorney, Agent, or Firm* — Boyle Fredrickson S.C.

(57) ABSTRACT

A medical pump for delivering medicament through an IV line to a patient may provide for awareness of the operator and operator authority limiting access by any individual to particular tasks of procedure review, pump programming, pump loading, patient set up, pump operation, and the like associated with the treatment provided by the medical pump. Identifying the operator allows the assignment of particular authority levels to the operators to ensure proper operation of the medical pump, and/or proper operators have made the necessary review to perform the necessary set up of the medical pump facilitating collaborative healthcare delivery. A record of operator intervention and authority levels may be logged to permit an automatic checklist process by the medical pump. Authentication process and pump operation parameters can be communicated through Near Field Communication (NFC).

15 Claims, 8 Drawing Sheets

Related U.S. Application Data

(60) Provisional application No. 61/770,757, filed on Feb. 28, 2013.

(51) Int. Cl.
*A61M 5/142* (2006.01)
*A61M 5/145* (2006.01)

(52) U.S. Cl.
CPC ............... *A61M 2205/6018* (2013.01); *A61M 2205/6054* (2013.01); *A61M 2205/6072* (2013.01)

(56) References Cited

U.S. PATENT DOCUMENTS

| | | |
|---|---|---|
| 7,785,463 B2 | 8/2010 | Bissler et al. |
| 8,515,547 B2 | 8/2013 | Mass et al. |
| 8,652,093 B2 | 2/2014 | Lee et al. |
| 2001/0021817 A1* | 9/2001 | Brugger et al. ............. 604/6.11 |
| 2002/0087116 A1* | 7/2002 | Hartlaub ......................... 604/65 |
| 2004/0167465 A1* | 8/2004 | Mihai ................... A61B 5/0002 604/67 |
| 2004/0193453 A1* | 9/2004 | Butterfield et al. ............. 705/2 |
| 2005/0277872 A1 | 12/2005 | Colby, Jr. et al. |
| 2007/0233050 A1* | 10/2007 | Wehba ................... A61M 5/142 604/890.1 |
| 2008/0147044 A1* | 6/2008 | Palmer et al. ................ 604/514 |
| 2008/0155258 A1* | 6/2008 | Obereiner ............. H04L 9/3226 713/168 |
| 2009/0099867 A1* | 4/2009 | Newman ........................... 705/2 |
| 2011/0092907 A1 | 4/2011 | Krogh et al. |
| 2012/0185267 A1* | 7/2012 | Kamen ................... G06Q 50/22 705/2 |

\* cited by examiner

MEDICAL PUMP WITH OPERATOR-AUTHORIZATION AWARENESS

CROSS-REFERENCE TO RELATED APPLICATION

This application claims the benefit of U.S. provisional application 61/770,757 filed Feb. 28, 2013 and hereby incorporated by reference and is a continuation in part of U.S. patent application Ser. No. 13/489,620 filed Jun. 6, 2012 and also incorporated by reference.

BACKGROUND OF THE INVENTION

The present invention relates to medical equipment such as bedside medical pumps for the delivery of medicines to patients, and in particular, to medical equipment that can authenticate, log and adjust its operation according to the authorization of an operator using the medical equipment.

Medical pumps, such as syringe pumps or peristaltic infusion pumps, are known for computer-controlled delivery of medication or contrast agents (henceforth medicaments) to patients over a period of time. Typically the medicament is delivered in a syringe (for a syringe pump) or a flexible bag (for peristaltic infusion pump, or ambulatory pump) that may be connected to an IV line attached to a needle for insertion into the patient. When a nurse or other healthcare professional ministering to the patient receives the medicament, the healthcare professional reviews the medicament description for correctness and enters the desired dose and rate into the pump. Other pump parameters such as alarm limits and the like may also be programmed at this time. The syringe or IV line must then be mechanically connected to the pump mechanism, the needle introduced into the patient, and the mechanism activated to begin pumping.

Advances in medical equipment design have greatly simplified the operation of such pumps permitting them to be used by a wide variety of environments and by different operators including not only trained healthcare professionals in a hospital environment but also in a home care setting by a visiting nurse or even by the patient themselves. U.S. patent application Ser. No. 13/488,841 filed Jun. 5, 2012, assigned to the assignee of the present application and hereby incorporated by reference, describes a system that allows the pump to be preloaded and preprogrammed by a pharmacist and/or skilled healthcare professional. These features are then locked out and optionally hidden from a home or other user who has access to a more limited set of control parameters for the pump.

It is likely that the future of healthcare services will see more specialization in the delivery of services. This may mean multiple different individuals will prepare, program and supervise the operation of medical pumps in a variety of different environments. While such division of labor can be highly efficient it creates a risk that important steps in the delivery chain may be omitted, particularly when no single individual has an overview of the process.

SUMMARY OF THE INVENTION

The present invention provides a medical pump which tracks multiple levels of authorizations of individuals working with the medical pump who are granted access to different features of the medical pump. Rather than a single password allowing control of critical pump features, operator-unique identifiers are used as linked to authorization levels. Different authorization levels provide access to different pump features, and the proper oversight by the necessary individuals is confirmed and logged for operation of the pump. This authorization data may be stored locally in the pump and remotely to permit a trade-off between immediate access to the data and long-term data security.

Specifically, the present invention provides a programmable medical pump having a housing holding a pump supported by the housing to receive an IV line and at least one sensor supported by the housing to monitor a flow of medicament through the IV line when received within the pump. An electronic computer communicating with the pump and sensor executes a stored program to:

(a) receive from a first individual data identifying the first individual;

(b) apply the data identifying first individual to a data structure linking individuals to authorization levels to determine a first authorization level for the first individual, where each authorization level provides a subset of permitted operations of the programmable medical pump;

(c) accept from the first individual commands related to operation of the programmable pump only if those commands are within the subset of permitted operations of the programmable pump of the first authorization level for the first individual; and (d) record the identity of the individual and at least one of a time of accepting commands from the first individual and the commands accepted from the first individual.

It is thus a feature of at least one embodiment of the invention to provide a medical pump that may distinguish and respond differently to different individuals depending on the authority of that individual. In this way, the invention may facilitate multistep processes for the delivery of medical care.

The electronic computer may be held within the housing and the data structure may be stored in the computer memory.

It is thus a feature of at least one embodiment of the invention to ensure availability of the medical pump even in situations where contact with a central database may not be possible.

The electronic computer may further include a network connection with a remote database and the data structure may be periodically synchronized with a remote database.

It is thus a feature of at least one embodiment of the invention to provide far central data logging and for the ready dissemination of authority data among many pieces of medical equipment.

The remote database may be an electronic medical record holding information about the medical history of the first individual or a drug dispense system database holding information about drugs to be dispensed, including but not limited to infusion parameters, and an associated patient.

It is thus a feature of at least one embodiment of the invention to provide a seamless integration of medical care delivered through medical equipment and the clinical patient record.

The electronic computer may further review the log to determine recorded activities of specific authorization levels before allowing some operations of the pump.

It is thus a feature of at least one embodiment of the invention to provide a medical device that can provide a degree of oversight over the proper completion of a multi-step delivery of medical care.

The pump may include a near field communication device and the first individual data may be received by the near field communication device.

It is thus a feature of at least one embodiment of the invention to provide a simple mechanism of identifying individuals operating on the medical pump and for confirming their proximity.

The data identifying the first individual may be received by a manually operated keypad comprising at least one of mechanical switches and a touchscreen keypad and/or may include biometric data acquired from the first individual using a biometric sensor.

It is thus a feature of at least one embodiment of the invention to provide a variety of flexible and secure techniques for identifying individuals and confirming their oversight of certain steps in the medical delivery process.

The data structure may include an authorization level not related to identification of the individual allowing some operations.

It is thus a feature of at least one embodiment of the invention to permit unregistered users to have limited control of the medical device, for example, for shutting the medical device down in certain circumstances or for completing tasks which require a low level of expertise.

The permitted operations controlled by the authority levels may relate to programming of the pump with respect to flow rate of the medicament, flow volume of the medicament, and/or identification of the medicament used with the pump.

It is thus a feature of at least one embodiment of the invention to ensure proper medical personnel oversight of critical pump features.

The process of authentication of the individual may be repeated whenever there is input from the user of commands changing operation of the programmable pump related a pump flow rate or volume or a medicament type.

It is thus a feature of at least one embodiment of the invention to prompt the user for identification when critical changes may be made or entered into a medical device during the delivery of medical care.

These particular objects and advantages may apply to only some embodiments falling within the claims and thus do not define the scope of the invention.

DETAILED DESCRIPTION OF THE PREFERRED EMBODIMENT

System Hardware

Figure 1:
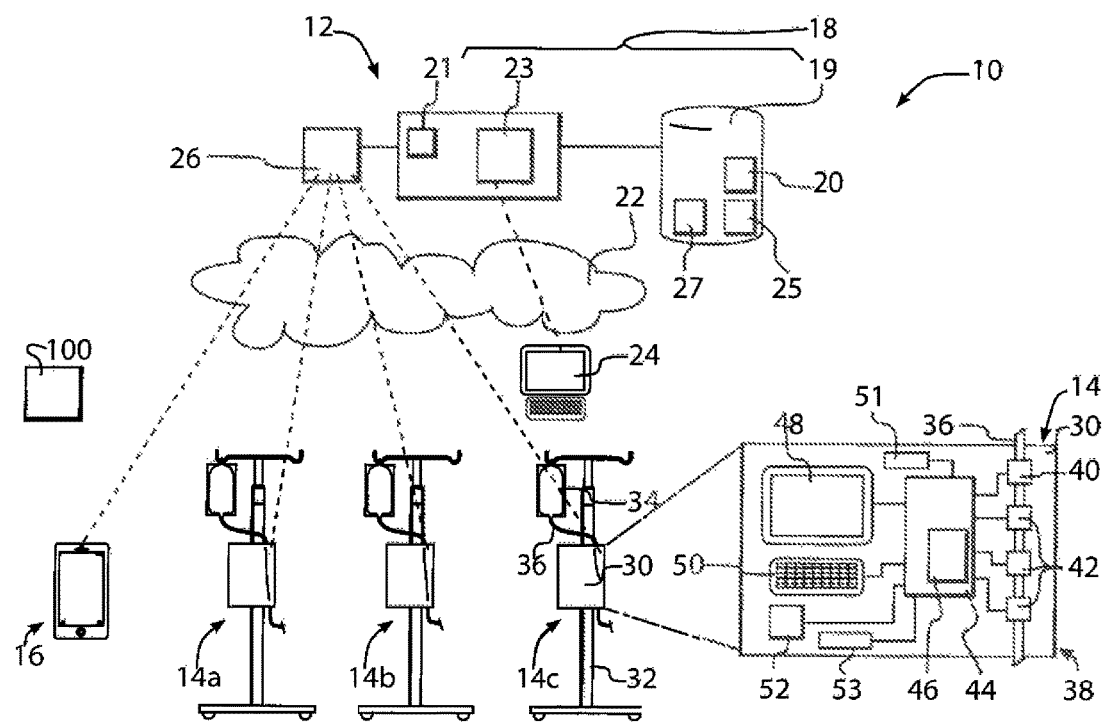
FIG. 1 is a block diagram of a medical pump system per the present invention providing wireless communication between medical pumps or a proxy and a standard medical database server showing various functional elements of the pump including an electronic controller executing a control program.

Referring now to FIG. 1, a medical infusion pump system 10 of the present invention may provide a file server system 12, one or more medical pumps 14a-14c, and one or more mobile devices 16 such as a cell phone, PDA, tablet or the like. Normally a mobile device will provide wireless communication complementing its mobile nature.

The file server system 12 may be part of a standard hospital electronic medical record or a drug dispense system(s) and may include a memory system 19, for example, providing a disk array or the like. The memory system 19 may provide part of a database system 18 holding medical information and patient records and may include an electronic database 20 providing infusion orders 68, for example, indicating medicaments and medical pump parameters for the delivery of those medicaments to patients as linked to particular patient names for identification. The database system 18 may further hold a remote authorization table 25 identifying individuals to particular authorization levels with respect to medical equipment together with a remote access log 27 recording the details of interaction between individuals and given medical equipment used with patients.

It will be understood that the database system 18 provides both file structures on physical non-transient medium and also a program or database engine for accessing that data. In this regard, the database system 18 may provide for a standard database interface, for example, using standard query language or a standardized API, and may further provide an interface accessible over a network. In one embodiment, this interface may allow communication between the standard database interface using network interface conventions, for example, as may be implemented under HTML, XML or other well-known standards. The database engine and portions of the database system 18 may be implemented by an electronic computer 21 being part of the file server system 12 executing a stored program 23 contained therein.

The file server system 12 may communicate with a wireless network circuit 26 or the like that may implement a portion of a network 22, for example, providing standard wireless communication protocols such as IEEE 802.11 (a)/(b)/(g)/(n). The wireless network circuit 26 may in turn communicate with corresponding wireless circuitry in each of the medical pumps 14*a*-14*c* as well as with mobile devices 16 as will be discussed below. The network 22 may also include physical media such as optical or electrical conductors.

The file server system 12 may connect via a network 22 with standard workstations 24 for use in a hospital or other healthcare setting. Such workstations 24, as is understood in the art, may access the database system 18 through a standard browser program to generate search queries and to receive query responses that may be used to extract particular information from the database system 18. Such file server systems 12 are normally pre-existing in a hospital environment as is necessary for the efficient management of patient information and hospital records independent of the present invention. The information of the electronic database 20, the remote authorization table 25, and the remote access log 27 may be populated or reviewed via the workstations 24 as is generally understood in the art. Data, from the file server system 12 may also be pushed to the workstations 24, for example on a regular schedule or as triggered by a new work order or change in status of a medical pump 14, without requiring searching or querying initiated at the workstation 24. One embodiment is that the information from the fileserver 12 can be displayed in a dashboard format at the workstation 24 to indicate a running status of individual medical pumps 14.

Referring still to FIG. 1, each medical pump 14 may provide, for example, a housing 30 that may be releasably attached to an IV pole 32, the latter that may support one or more bags of IV fluid 34 thereupon. The IV fluid 34 may be a saline solution or any of a number of administered medicaments. The term medicament generally contemplates a variety of materials that may be introduced to the patient including saline solution, nutrients, plasma, antibiotics or other medicaments, and chemotherapy agents.

An IV tube 36 may pass from the IV bag through a pump section 38 of the housing 30 of the medical pump 14 to be received by a peristaltic pump element 40 and one or more sensors 42, for example, including sensors for pressure of the IV fluid, flow rate of the IV fluid, air inclusion within the TV fluid, proper seating of the IV tube, and the like, all generally understood in the art. The IV tube 36 may then pass out of the pump section 38 to a needle assembly (not shown) or other means (such as a catheter) to attach to a patient.

Each of the pump element 40 and sensors 42 may connect to an internal computer 44 and execute a stored program 46 to provide control of the pump element 40 according to the program 46 and according to the readings of the sensors 42.

The computer 44 may also communicate with user interface elements including a display screen 48 and a keypad 50 or the like, the latter including being provided by membrane switches, a touchscreen or the like. The user interface elements may further include a biometric sensor 51 being any of a number of different biometric sensor types known in the art including, for example, a fingerprint sensor, a camera providing face recognition or iris scanning and a microphone providing for voiceprint identification.

It will be appreciated that the user interface elements of screen 48, keypad 50, wireless network circuit 52 and biometric sensor 51 may be implemented by a mobile device 16 such as a smart phone or tablet (henceforth smart device) securely linked with the computer 44, for example, through the near field communication device 53 so that its own keyboard, display, and biometric sensing elements may be used. As used herein, near field communication refers to a wireless technology operating at a distance of four centimeters or less and not operating at distances of greater than approximately one meter.

Near field communication technology includes both passive technologies, for example, working with circuits that do not have power but that scavenge power from a near field communication signal in the manner of an RFD tag, and active technologies such as two powered devices communicating with each other using near field communication protocols and hardware. Critically, near field communication requires physical proximity between the communicating devices. In some cases, near field communication may include optical communication, for example, barcode reading; however, the invention contemplates primarily radiofrequency near field communication devices communicating over radio waves in the radio spectrum or low-frequency magnetic communication. Generally near field communication devices may include Bluetooth communication.

In this situation, a single mobile device 16 such as an iPhone or Android operating system phone is linked to the medical pump 14 in a secure manner, for example, through corresponding keystroke commands on the keypad 50 and the mobile device 16 creating a Bluetooth linkage and the process steps described above implemented through the mobile device 16.

It will be appreciated that proper security protocols may allow long-distance linkage of the mobile device 16 and medical pump 14, for example, through a wireless network or the like.

In this regard or for other purposes, the computer 44 may communicate with a wireless network circuit 52 similar to the wireless network circuit 26 described above for communication over the network 22. The computer 44 may also communicate with a near field communication device 53.

In an alternative embodiment, one or more of the medical pumps 14 may be a "syringe pump" or an ambulatory pump having similar features to the infusion pump described above, for the delivery of medicines and the like.

Figure 2:
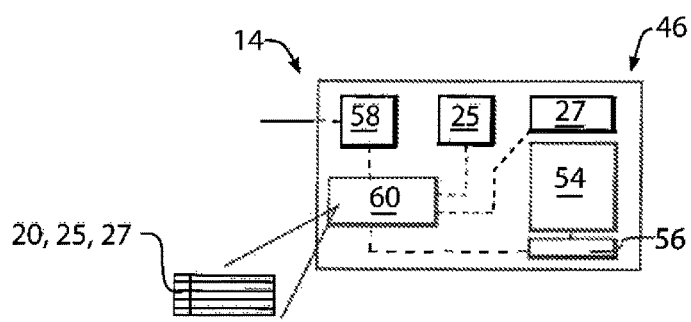
FIG. 2 is a block diagram of principal structures of a control program of the medical pump providing an ability to navigate the wireless network and to communicate with a remote patient record database.

Referring now to FIG. 2, in a first embodiment, the program 46 may provide for a number of program elements including generally an operating program 54 such as provides for the normal operation and control of the medical pump 14. The operating program 54 may communicate with user interface routines 56 allowing the receipt of data from and transmission of data to the user interface formed by display screen 48 and keypad 50. Generally, the operating program 54 may execute a user-defined protocol to deliver medicament by controlling the pump elements 40 to provide a controlled delivery of medicament according to a time schedule indicating flow rates, medicament name, and delivery volume. The operating program 54 also handles authentication and data logging as will be described.

The program 46 may further include a network stack 58 for communication with the wireless network circuit 52 for receipt of data therefrom and transmission of data thereto. The network stack 58 may communicate with a database access routine 60 that may access the electronic database 20, the remote authorization table 25, and the remote access log 27 as stored in the database system 18. The database access routine 60 may also communicate with the user interface routines 56 for receiving instructions therefrom related to queries or selection among query results and for displaying the results of queries and the like as will be described. In addition, the database access routine 60 may access a local authorization table 25 and local access log 27 as will be described.

Data Structures

Figure 3:
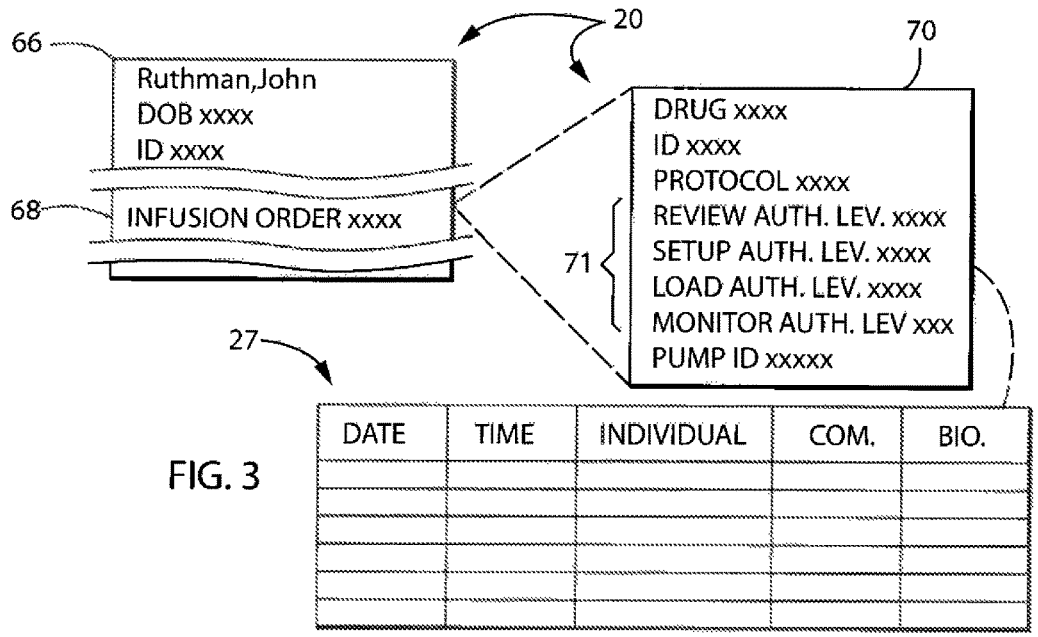
FIG. 3 is a simplified diagram of a data structure of an electronic medical record for an individual patient or drag dispense system database linked to an individual showing an infusion order that provides multiple tasks associated with authorization levels and further linked to an activity log of a given pump.

Referring now to FIGS. 1 and 3, the electronic database 20 may provide multiple patient medical records 66, each associated with a given patient and for example, identifying a patient by name, date of birth, and a patient identification number. In FIG. 3, the data is generally indicated by a series of x symbols. Generally, the electronic database 20 will provide a medical history of that patient including medical conditions and treatments and may also include pending physician orders, for example, an infusion order 68 having a unique order identification number or may be a drug dispense system database holding information about drugs to be dispensed.

The infusion order 68 may be linked to infusion data 70, for example, contained in a separate table and providing information relevant to an infusion operation to be performed by a medical pump 14. While a number of different data formats are envisioned, the infusion data 70 will generally include an identification of a medicament for infusion, a link to the patient identity patient number, and a protocol for delivery of the drug, for example, flow rate, delivery volume, and timing. In particular, the infusion data 70 will describe one or more tasks 71 that must be implemented for completion of the order. Each task 71 will be assigned to an authorization level indicating generally a class of individuals who are authorized to complete that task 71. For example, the tasks 71 may include the review of the infusion order for medical correctness typically requiring an authorization level limited to a physician or the like. In some cases, for example, for chemotherapy infusions, the task 71 may require two individuals of the same authority to each supervise the other contemporaneously. Additional tasks 71 may include set up of the medical pump 14, for example, programming data into the medical pump 14 (e.g. flow volume and flow rate), physically loading of the medical pump 14 by installing the proper medicament in the medical pump 14, and a monitoring of the pump operation during delivery of the medicament. Normally, the authorization levels necessary for each of these tasks 71 will change depending on the particular situation. For example, a chemotherapy infusion might require a higher authorization level for supervision, including only healthcare professionals, whereas an infusion suitable for home care might not require a healthcare professional for supervision but only a competent adult. A copy of the infusion data 70 and tasks 71 may be read by the medical pump 14 and stored therein for ready availability.

The infusion data 70 may be associated with a remote access log 27 unique to a particular medical pump 14 that may log completion of the tasks 71 associated with the infusion order 68 and the infusion order data 74. This remote access log 27 may also be downloaded to the medical pump 14.

The remote access log 27 may identify, for example, a date and time and individual completing the task as well as the instructions (button presses, etc.) provided to the medical device in the completion of the task when such commands are relevant, for example, in the programming of the medical device. The remote access log 27 may also record various environmental variables, for example, the type of medicament, when that data is input automatically.

In this regard, the remote access log 27 serves two purposes. First, it provides a record of the individuals involved in each step of the medical procedure with the medical pump 14 for accountability. Second, it provides data that can be used for an automatic check-listing process that ensures proper completion of the necessary steps of an infusion order that have been performed. The provision of an access log 27 contemplates that other information may be recorded, for example, when biometric sensing is used as described below, for example, the user's photograph or biometric data.

Figure 4:
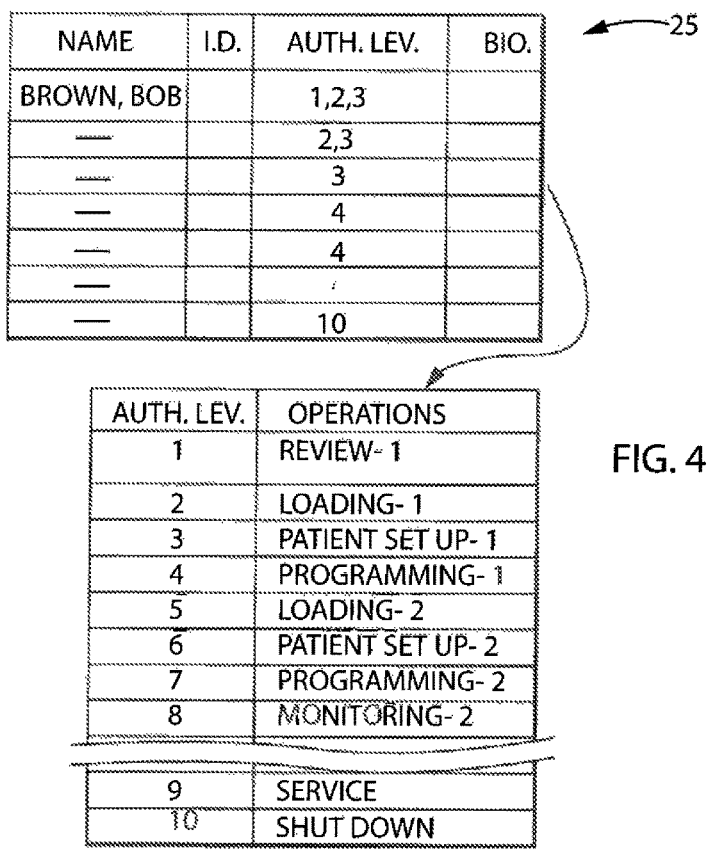
FIG. 4 is a simplified diagram of a data structure of an authorization table linking specific individuals to authorization levels and authorization levels to allowable operations using the medical pump.

Referring now to FIG. 4, the remote authorization table 25 links particular named individuals and their unique individual IDs to at least one authorization level and possibly several. Thus, for example, a physician might have an authorization level I which could match the task 71 of reviewing the infusion order but could also be authorized for lower authorization levels that do not require a physician. The individuals listed in the authorization table may include healthcare professionals such as physicians, or nurses or aides and may include non-healthcare professionals such as family members, friends or the like. Each authorization level may be associated with permitted operations related to medical treatment using a medical pump 14.

As noted above, an authorization level of "one", for example, may permit a "signing-off" of an infusion plan whereas an authorization level of "two" may permit loading of an infusion machine with a medicament including, for example, installing a syringe in a syringe pump or medicament in an IV infusion pump. As a continued example, an authorization level of "three" may permit preparation of the patient including introduction of needles and the like. An authorization level of "four" may be suitable for patient monitoring during the infusion process.

Each of these levels may be subdivided with respect to different types or classes of medicament. For example, saline and nutrition solutions may provide a first subdivision of authorization levels, painkillers a second subdivision of authorization levels and chemotherapy agents of third subdivision of authorization levels reflecting the different knowledge and level of supervision required of each of these tasks. Different individuals may be linked to different and only some of the subdivisions of an authorization level.

These authorization levels are offered as an example and can be easily customized for different situations. In some circumstances, a single individual can be authorized to undertake multiple tasks 71; however, program 54 may enforce the use of different individuals for different tasks regardless of the authorization level for some important tasks that require multiple levels of oversight.

The authorization levels may include a service level which allow servicing or modification of the medical pump 14, for example, needed for repair, inspection or calibration, as will be discussed below. The authorization levels may also include a default level allowing some access to the medical pump 14, for example, stopping the operation of the medical pump 14, when the operator cannot be identified either because there has been no operator identification input or the operators are not listed in remote or local authorization table 25.

Some authorization levels may require the individual to be in proximity with the medical pump 14, for example, as determined by NFC communication with a device linked to the individual.

Figure 5:
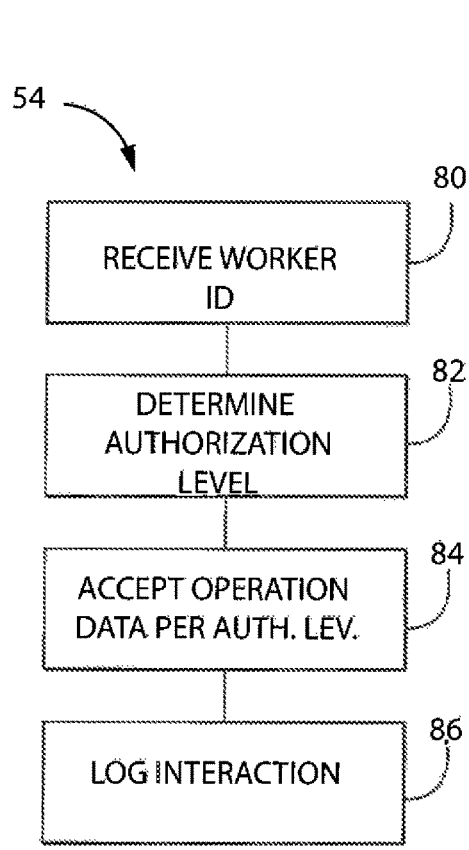
FIG. 5 is a flowchart of an authorization routine executed by the medical pump upon interaction with the medical pump by medical or other personnel.

Referring now to FIGS. 1 and 5, multiple individuals will interact with the medical pump 14 during the implementation of an infusion order. Program 54 may enforce a standard protocol with respect to these interactions. As indicated at process block 80, as a first step in each interaction, the worker interacting with the medical pump 14 must be identified positively. Typically, this identification is by a close range interaction of the individual with the medical pump 14 such as occurs naturally during the interaction between the individual and the medical pump 14, for example, during programming or loading of the medical pump 14. In the simplest implementation, the individual may enter a unique ID and the password, for example, through the keypad 50 or through a device securely linked to the computer 44, for example, through a near field communication link of NFC device 53 to a user device as will be discussed further below. The user identification or password may be a number, a text string or the like.

The invention contemplates that this identification may be provided all or in part, instead, by biometric identification by biometric sensors 51. As noted, the biometric sensor 51 may make use of a variety of different sensor techniques to establish a characteristic inherent to the individual using the medical pump. This biometric data may be stored in the remote or local authorization tables 25.

Generally a combination of two identification techniques will be used for example, a password and biometric data, or a user name and biometric data, or the like. The invention also contemplates that user identity may be provided by a unique article held by the individual, for example, an RFID tag with the individual's identity, coupled with a password entered by the user.

Once the individual has been positively identified, the remote authorization table 25 is interrogated as indicated by process block 82. Generally, this authorization process reviews the remote authorization table 25 held directly in the file server system 12 so as to ensure reference to an up-to-date centralized record system. Nevertheless, if the remote authorization table 25 is not available, reference may be made to the local authorization table 25 stored in the medical pump 14 to eliminate any possible delay if there is a wireless communication interruption. This local authorization table 25, as well as local access log 27, are synchronized with remote authorization table 25 and remote access log 27 when wireless communication is available and an error may be indicated to the user of the medical pump 14 if communication for synchronization purposes is not available on a regular basis so as to indicate possible staleness in the data of these tables.

Once the authorization levels have been determined, then at process block 84, interaction with the user and the medical pump 14 is permitted within the scope of the authorization. Thus, for example, if the individual has authorization to set up the machine, machine set-up data, for example, drug name, flow rate, and delivery volume pressures and the like, may be entered by the user into the medical pump 14. This may be typically performed using the keypad 50 but may also be performed with downloads from mobile device 16 held by the individual and securely linked the medical pump 14, for example, through near field communication of NFC device 53. In this regard, the mobile device 16 may serve as a wireless conduit for the medical pump 14, allowing remote communication with the medical pump 14 to program, monitor, or control the same. This can be particularly useful in the context of home treatment, where the treatment timing may be logged, and the pump setting monitored or changed remotely through the mobile device 16 as linked to the medical pump 14.

At the conclusion of this interaction by an individual, the data is logged as indicated by process block 86. This logged data is generally written both to the local access log 27 and the remote access log 27 to keep these logs in synchrony but the invention allows writing only to local access log 27 in the event of a loss of communication with the file server system 12 for subsequent synchronization.

In some cases, the interaction with the user may be done remotely, for example, in the review of the infusion order. In this case, the necessary identification of the individual may be accomplished remotely, for example, through a secure terminal connection that provides for biometric sensing or the entry of the necessary data. This identification may be linked to the desired data (for example, an indication of approval of the infusion order), for example, through public-key encryption to prevent tampering and typically will include a timestamp that limits the effective duration of this authorization.

Figure 6:
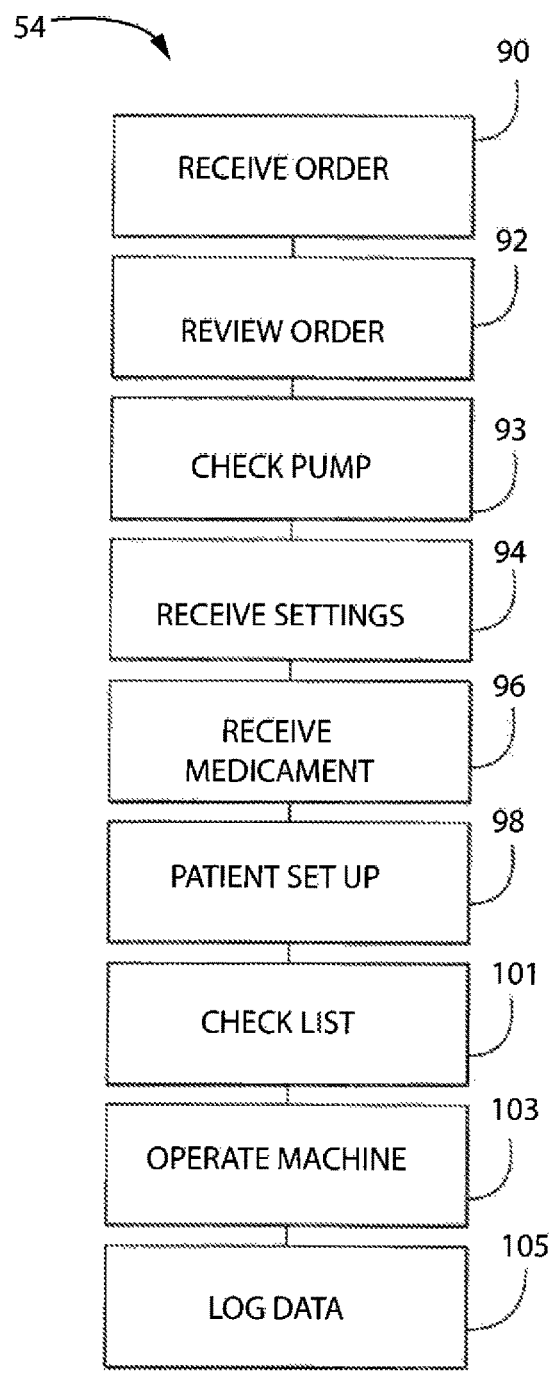
FIG. 6 is a figure similar to that of FIG. 5 showing a flowchart of a typical infusion medical procedure executed by the medical pump.

Referring now to FIG. 6, the process of FIG. 5 may be repeated for multiple stages beginning with the receipt of an infusion order as indicated by process block 90 that may be loaded into the medical pump 14. This infusion order may be entered manually through the keyboard or preferably through wireless download from the file server system 12. This infusion order includes the data of infusion data 70 discussed above and provides the machine with important information, that will be used to authenticate and monitor its operation.

At process block 92, a review of the proper loading of the infusion order may be received by an individual with the necessary authorization level following the procedure described, with respect to FIG. 5.

At process block 93, the correct identity of the type of the medical pump 14 and serial number of the medical pump 14 which may be associated with a particular patient room or patient may be confirmed as will be discussed below. As a part of this confirmation process proper functioning and service of the medical pump 14 may be confirmed.

At process block 94, pump values may be programmed, for example, flow rates, delivery volume and the like. At process block 96 the medicament may be loaded and confirmed by an authorized individual and/or automatically through near field communication as will be discussed below.

Figure 12:
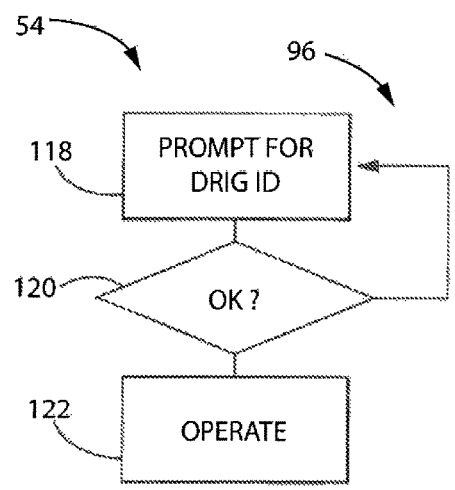
FIG. 12 is a flowchart implemented by programming of the portable device and/or the medical equipment using near field communication to validate medicament delivery.

Referring momentarily to FIG. 12, as part of process block 96, at process block 118, the user may be prompted to verify the drug in IV bag 114 through near field communication by physically moving the mobile device 16 in proximity to the tag 112. If information read through the NFC port 110 from tag 112 matches that of the order loaded at process block 116, as indicated by decision block 120, the program may proceed to process block 122 for additional authentication steps or operation of the pump to deliver the medicament.

At process block 98 the patient may be set up and the medical pump 14 readied for operation.

At process block 101, the checklist of tasks 71 of the infusion order data is used to confirm that each of the steps of process blocks 92, 94, 96, and 98 has been successfully completed up to the point of actual drug delivery.

At this point as indicated by process block 103, drug delivery may be conducted as initiated and monitored by an authorized individual. The monitoring process may require, for example, periodic entry of data to the medical pump 14 indicating the presence of that individual.

At process block 105, the remote access log 27 and local access log 27 may be updated as available.

At each of these steps the program 54 may conduct a consistency audit comparing the information from the received order 70 with other data provided by different individuals. For example, the medicament listed in the received order may be compared against the actual medicament loaded at process block 96. Likewise the protocol information of the infusion data 70 may be used to check the patient program settings, and the patient identification, during patient setup of process block 98, may be compared against a patient ID linked through the infusion data 70 to the given patient medical record 66. In this way authorization of the individuals performing the tasks and a check of those individuals with each other is performed.

During operation of the medical pump 14 as indicated by process block 103, any change in parameters associated with process blocks 92, 93, 94, 96, and 98 may trigger a repeat of those process blocks with respect to authentication of the individual making the changes per FIG. 5. An exception to this requirement is any change that might be necessary for safety reasons such as disabling the medical pump 14.

During the operation of the medical pump 14 per process block 103, the wireless network 22 and the established connection may be used to report out particular alarm conditions and operating status of the machine. The status may include, for example, problems detected in the delivery of the drug, for example, by sensors 42 described above with respect to FIG. 1, the activation of alarm conditions or the like. Other remote control of the medical pump 14 through the network is also possible.

Figure 8:
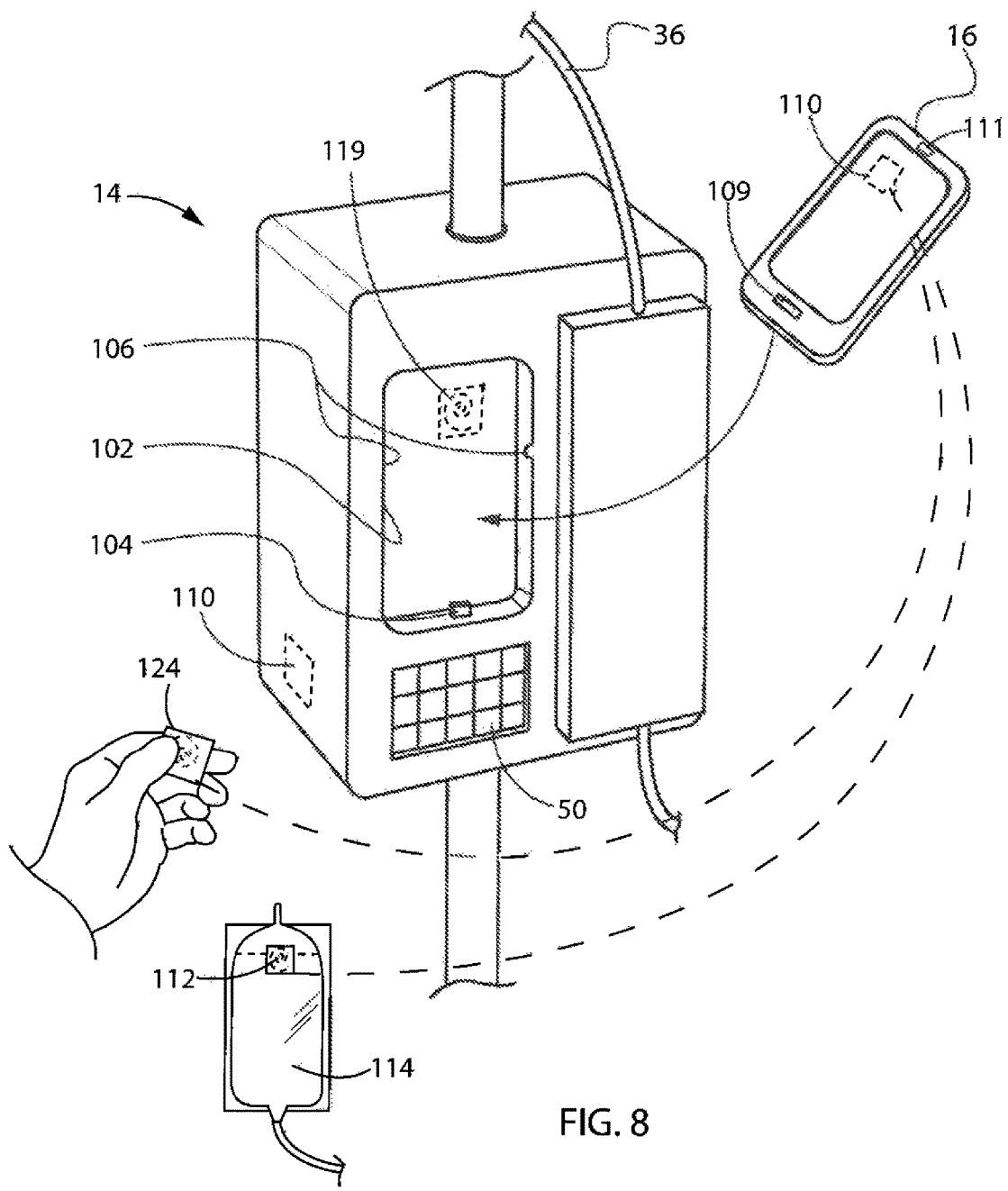
FIG. 8 is a fragmentary perspective view of an infusion pump per the present invention providing a socket for receiving a smart phone or the like therein to provide all or portions of the electronic computer and biometric sensing elements.

Referring now to FIGS. 1 and 8, as noted above, in an alternative embodiment, limitations in the computational or hardware capability of the medical pump 14 (for example, needed to support the network connection, query generation and mapping process) may be accommodated through the use of mobile devices 16 typically nearby the medical pump 14 and communicating therewith either through a wired or wireless connection. Alternatively, the mobile devices 16 may be integrated into the medical pump 14, for example, in a docking cradle with an interfacing electrical connector removably holding, for example, a tablet or smart phone, as described below. The mobile devices 16 may also provide a processor executing a stored program implementing many of the functions of program 54, the network stack 58, the database access routine 60, the local authorization table 25 and local access log 27. The mobile device 16 will include an active near field communication transceiver, for example, as currently available on Android™ and BlackBerry phones.

Agent Device

Figure 7:
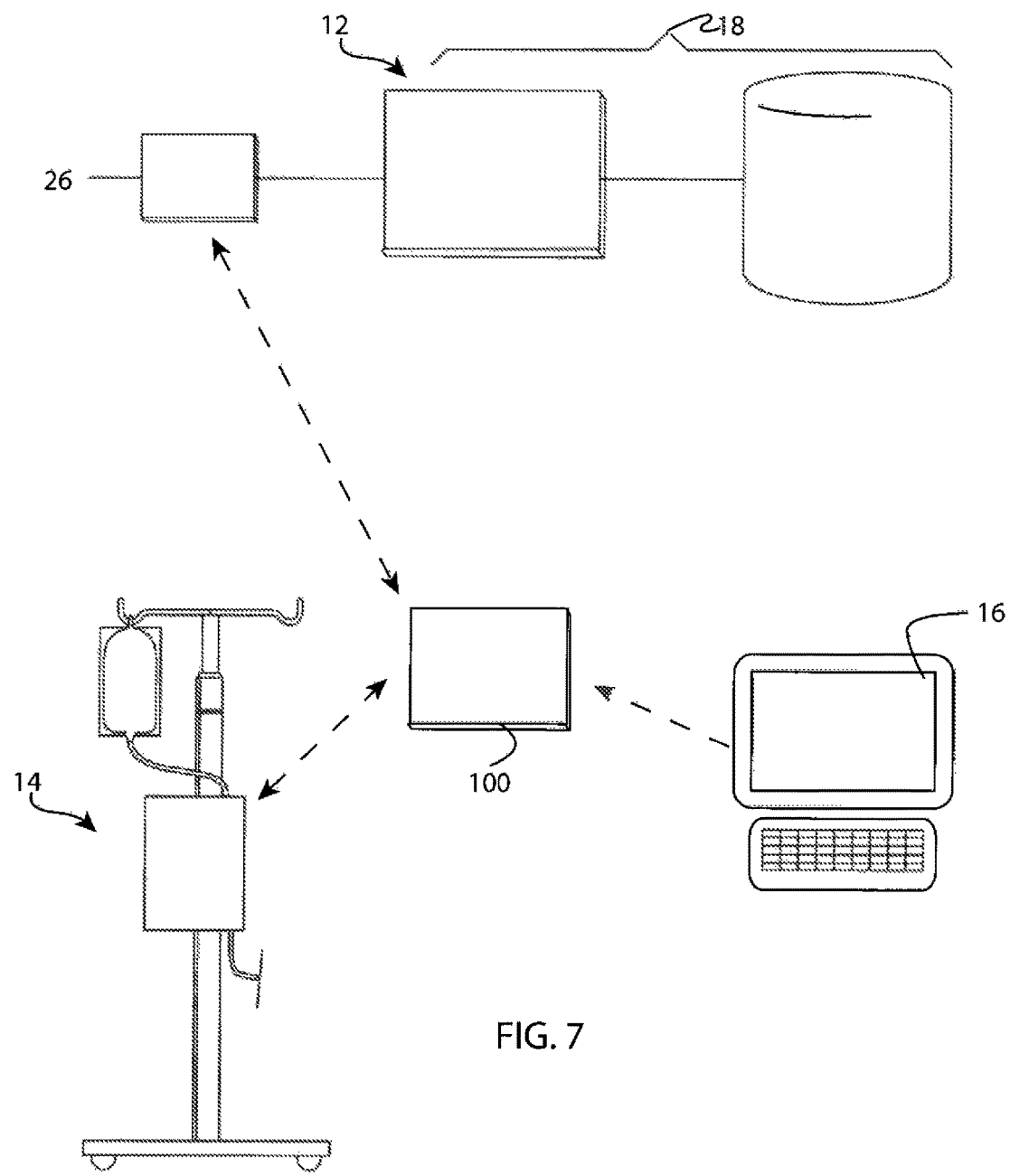
FIG. 7 is a figure illustrating an agent device wirelessly communicating with a medical pump.

In the above examples, the communication between the medical pump 14 and the file server system 12 may be conducted through an agent device 100, for example, providing a standard address preprogrammed into each of the pumps 14. As illustrated in FIG. 7, the agent device 100 may then implement a router type function to communicate with the necessary address of the file server system 12 and database system 18. In this way, each of the pumps 14 may be preprogrammed with only the address of the agent device 100, and the agent device 100 may be programmed independently, for example, using a more convenient user interface and a more powerful processing circuit. For example, the agent device 100 may be a standard desktop computer or the like including, for example, a computer implementing the mobile devices 16. The agent device 100 may likewise implement some of the steps of the mobile devices 16. It should be understood that the agent device 100 and mobile device 16 are optional and the medical pump 14 itself can have the capability of executing the functions provided by the agent 100 and mobile device 16.

Significantly, the agent device 100 may be used to provide for the communication of data between the mobile devices 16 and the medical pump 14 when the mobile devices 16 are used. For example, in one embodiment, the transfer of data to the medical pump 14 from the server system 12 (and hence from the database system 18) may be received by the mobile devices 16 and transferred to the agent device 100 and then to the medical pump 14. Alternatively, the data from the server system 12 intended for the mobile devices 16 may be intercepted by the agent device 100 to be transmitted to the medical pump 14. In this latter case, all communications via the mobile devices 16 may pass through the agent device 100. Again this provides a uniformity of communication addresses for the medical pump 14 and agent device 100 and further allows the existing hospital file server system 12 to be used without modification or substantial modification. This elimination of the need to modify the existing information infrastructure of the hospital both simplifies the use of the present invention and allows its incremental adoption without the need to overcome substantial fixed capital costs.

Near Field Communication Authentication

Referring now to FIG. 8, the mobile devices 16, in the form of a smart phone or tablet, may be received within a socket 102 formed in a front panel of an infusion medical pump 14 to engage with an electrical connector 104 on the infusion medical pump 14 within the socket 102 and providing direct electrical communication between the medical pump 14 (e.g. the computer 44) and the mobile devices 16. As is generally understood in the art, a tablet and/or smart phone will generally have wireless capabilities, a data exchange socket, and full user interface including typically a touchscreen display driven by an internal processor having local memory and biometric sensors, for example, fingerprint sensors 109 or a camera 111 suitable for facial recognition or the like. The socket 102 may further provide mechanical retention elements 106 releasably holding the mobile devices 16 therein. Optionally, the communication between the pump and the mobile devices 16 may be wireless, for example, by a Bluetooth connection, thus the socket 102 and electrical connector 104 are optional.

As so installed in the medical pump 14, the mobile devices 16 may present a front facing data entry and display screen 108 (for example, a touch screen) allowing the user to enter the search strings described above. In this regard, it will be appreciated that the mobile devices 16 may communicate wirelessly with the file server system 12 through the wireless network circuit 26 and may provide a conduit for the received programming data passed from file server system 12, through the mobile devices 16, to the medical pump 14 through the connector 104.

A rear of the socket 102 may include a passive or active NFC port 110 that may be read by active near field communication circuitry within the mobile device 16 to authenticate that the programming data in the mobile device 16 is being applied to the proper medical pump 14. This is done by comparing machine identification information in the NFC port 110 of NFC device 53 with similar information held in the programming data received by the mobile device. The NFC port 110 holds a value that uniquely identifies a single medical pump 14 and optionally, in addition, a class of pumps.

Alternatively or in addition, the information exchanged by near field communication may establish a connection (such as a Bluetooth connection) between the mobile device 16 and the medical pump 14 preventing interference from other mobile devices 16 or mistaken acceptance of instructions from those mobile devices 16 which is particularly important for wireless communication. This connection allows subsequent removal of the mobile device 16 from the socket 102 while still allowing some control capabilities as will be described. By employing a mobile device 16 as the user interface to the medical pump 14, a more consistent and convenient user interface may be provided as controlled by the mobile device 16.

The medical pump 14 and/or the mobile device 16 may also provide for an active near field NFC port 110 positioned on another surface of the housing of the medical pump 14 either of which may be used, for example, to read a passive near field communication RFID tag 112 on an IV bag 114. In this way, programming in the medical pump 14 or in the mobile device 16 may confirm loading of the proper medicine into the IV medical pump 14. The near field RFID tag 112 may hold a value identifying the drug and amount of drug in the IV bag 114.

Referring still to FIG. 8, the near field NFC port 110 on either the medical pump 14 or the mobile device 16 may also be used in conjunction with a security tag 124, for example, held by service personnel or authorized healthcare personnel providing a form of user identification discussed above. Normally, a second identification is required, in this case in the form of a personal identification number (PIN) entered into the mobile device 16 or through the keypad 50 of the medical pump 14.

This form of identification using a security tag 124 may be preferred for establishing user identity with respect to service authorization levels allowing access to the machine and its diagnostic information by service personnel. One feature possible with this authorization level is the resetting of a service clock. The program 54 may keep a running total of the operating time of medical pump 14 or the total amount of volume of medicament pumped since the last resetting of the service clock which may be accessible to service personnel, for example, on display screen 48. The term service, clock refers simply to a log memory value in the computer keeping track of time or cumulative volume infused A warning of necessary service may be broadcast, for example, wirelessly when service is required based on the volume of medicament pumped or the last resetting of the service clock. This wireless data may be received by the file server system 12 in the same fashion as any error and by the program 54 to provide a display on display screen 48 and optionally to lockout further operation of the machine until services are performed. For example, service may be required after a certain number of machine operating hours in the same way that services are indicated in an automobile after a predetermined number of odometer miles.

Figure 9:
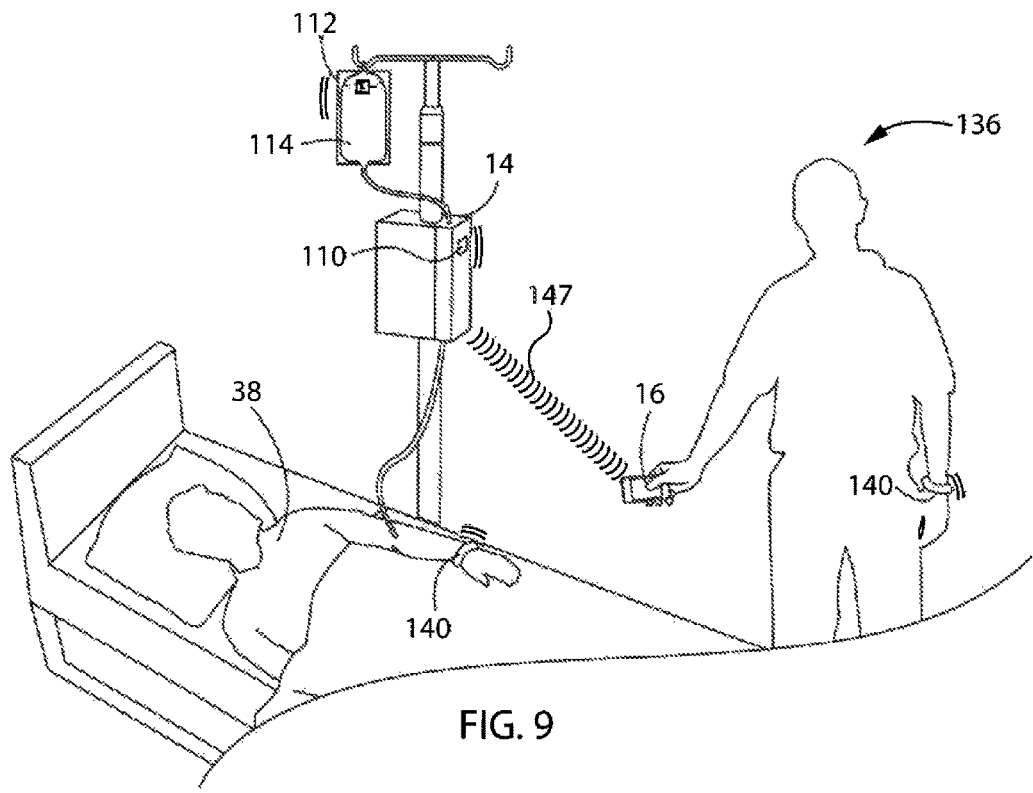
FIG. 9 is a perspective view of a typical bedside environment showing multiple treatment components having near field communication devices, the components to be coordinated for treatment of the patient.
Figure 11:
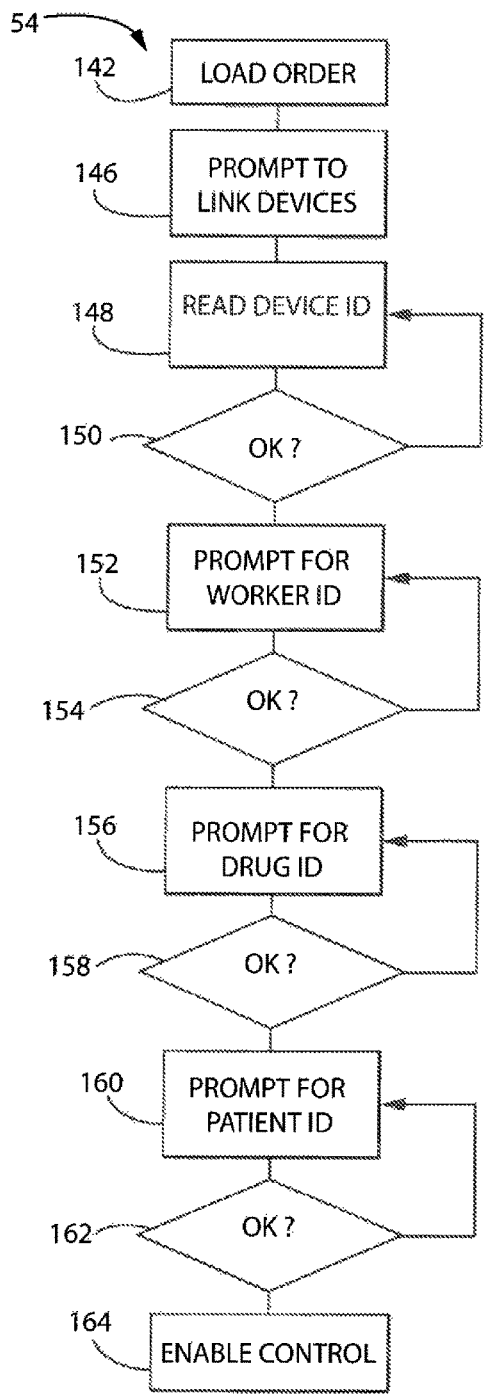
FIG. 11 is a flowchart of a program implemented by a portable device and/or the medical equipment for coordinating treatment using the portable device and the medical equipment.

Referring now to FIGS. 8, 9 and 11, the use of near field communication (NFC), including radio frequency identification (RFID) tags and barcode tags that may be only read at close proximity, allows for a highly reliable authentication process that confirms proper identities of all the resources necessary for treatment of the patient. These resources include the proper healthcare professional 136 supervising the medical treatment, the proper medical pump 14, the proper drug in IV bag 114 and the correct patient 138. In this regard the healthcare professional 136 and the patient 138 may both have, for example, wristbands 140 holding near field communication devices. A similar NFC port 110 (active or passive) may be located on the medical pump 14 as described above and on tag 112 on the IV bag 114.

In this coordination process, as indicated by process block 142 a infusion order 68 may be loaded into one or both of the mobile device 16 and medical pump 14 as described above with respect to FIG. 6. The mobile device 16 may then be linked or paired to the medical pump 14, for example, using the process of near field communication between the mobile device 16 and NFC port 110 described above with respect to FIG. 8 as indicated by process block 146. This linking process allows the device ID unique to the medical pump 14 to be obtained as indicated by process block 148.

When this linking process is complete, the medical pump 14 and mobile device 16 may communicate by a non-near field communication link such as a Bluetooth communication channel 147 operating at a substantial distance to allow movement by the healthcare professional 136. This linking allows control of the medical pump 14 by the mobile device 16 in a convenient manner and the movement of the mobile device 16 about the treatment area for authenticating other treatment elements.

The identity of the medical pump 14 obtained during the linking process is then compared against the class of acceptable pump types (or an exact pump ID) contained in the infusion order 68 as indicated by process block 150. If the pump type or ID is appropriate, the particular medical pump 14 is recorded and the program proceeds to process block 152 prompting the user to identify him or herself. This identification process employs near field communication, for example, between the wristband 140 of the healthcare professional 136 and the mobile device 16, the latter of which may move between each element for this identification process relying on near field communication.

Figure 10:
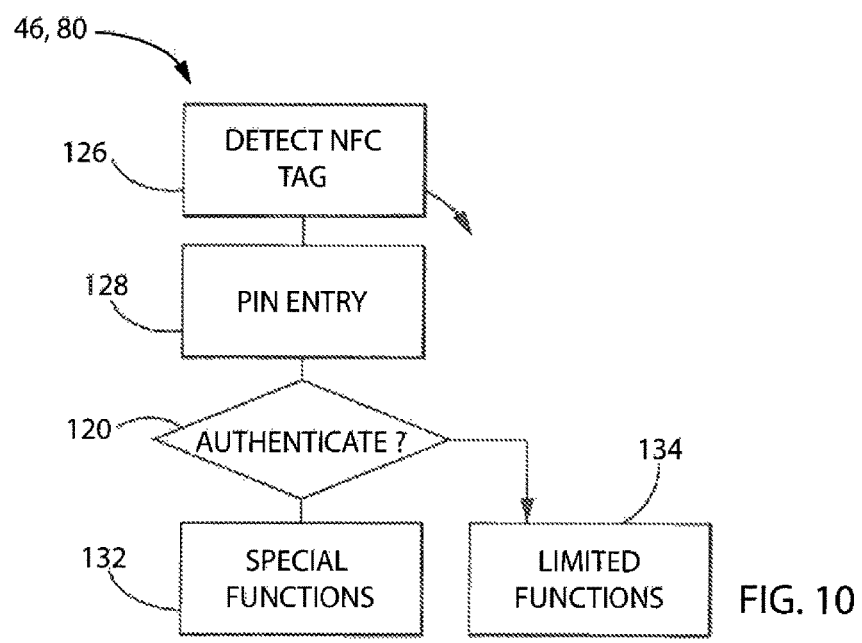
FIG. 10 is a flowchart of a program executed by the medical equipment for unlocking special programming features based on communication with a near field communication tag.

Referring now to FIG. 10, program 46 or 80 may generally detect the presence of the security tag near NFC port 110 at process block 126. Normally, a second identification is required as indicated by process block 128, for example, in the form of a personal identification number (PIN) entered into the mobile device 16 or through the keypad 50 of the pump 14. If data read from the security tag 124 and entered at process block 128 matches a set of stored authorized values in the pump 14, as indicated by process block 130, then the program moves to process block 132 and secure features of the pump may be accessed. Depending on the implementation, the PIN entry may not be necessary. Such secure features may include overriding of pump limit or default values or obtaining diagnostic information that may be used by service personnel. Such secure features may further include general authorization to use the pump or start the pump or change the programming of the pump useful to further control of authority among medical staff (as will be described below) to those individuals in proximity. If authentication is not provided then at process block 134 a limited operation of the pump 14 may be provided, for example, limited to reading out pump parameters and stopping the pump 14.

If the healthcare professional has authority, as indicated by the information of the loaded infusion order 68 at process block 142, and as determined by decision block 154, then the program proceeds to process block 156 and the user (typically the healthcare professional 136) is prompted to confirm the identity of the drug (drug type and volume) by scanning tag 112 of the IV bag 114 with mobile device 16.

If the drug type is correct, as being of the class and description defined by the infusion order 68, as determined by decision block 158, the program proceeds to process block 160 and the user is prompted to confirm that the proper patient is connected to the medical pump 14 by again moving the mobile device 16 to the wristband 140 of the patient 138 for near field communication.

If this final confirmation of the identity of the patient 138 against the infusion order 68 is complete, as determined by decision block 162, control of the medical pump 14 by the mobile device 16 is provided at process block 164. The control will normally involve the exchange of unique identification information during each control message as was established during the linking of process block 146 and will permit the mobile device 16 to be placed in the socket 102 of FIG. 8 or more generally used in a roaming configuration as held by the healthcare professional 136.

It will be appreciated that the physical act of moving the mobile device 16 to touch each of the elements of the medical treatment in sequence provides a highly robust assurance that the proper patient is being treated with the proper equipment and the proper drug under the supervision of the correct personnel. Confirmation of this information may be reported to a central database by the mechanisms described above.

In application, for example, the mobile devices 16 may be used either free from the medical pump 14 or when connected to the medical pump 14 to make the connections to the file server system 12 and to obtain the necessary pump programming information.

Figure 13:
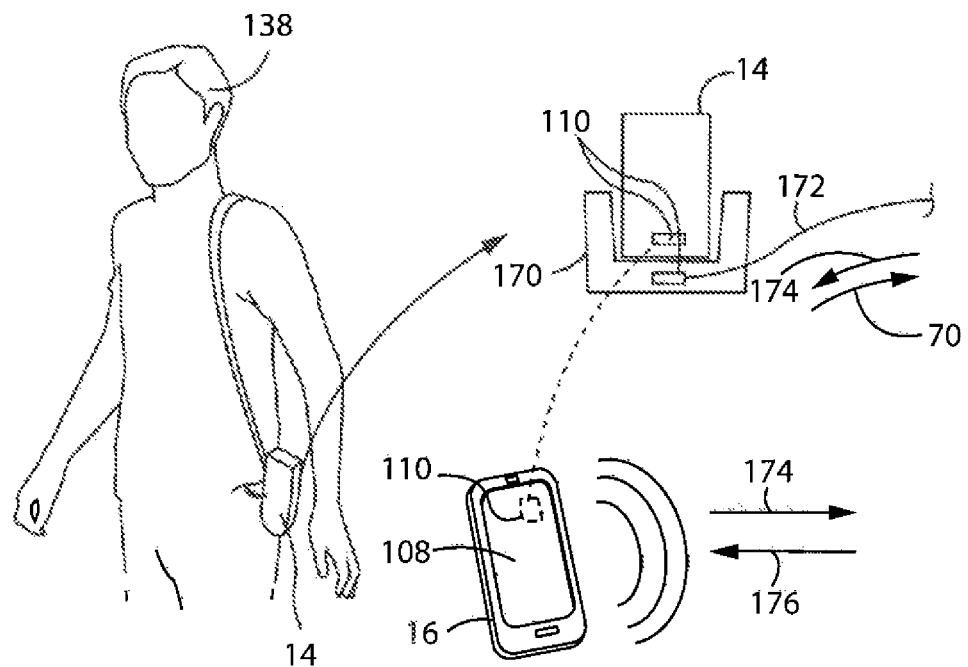
FIG. 13 is a simplified diagram of a portable infusion device that may be received in a cradle or may communicate with a portable cell phone or the like for obtaining programming information and transferring log performance information to a remote computing system.

Referring now to FIG. 13, the above-described principles may also be applied in providing communication between a portable infusion medical pump 14 of the type that may be earned by an ambulatory patient 138 and a remote source of programming. The infusion medical pump 14 in this case provides for an active NFC port 110 of the type described above with respect to FIG. 8 in order to exchange data with an adjacent NFC port 110, for example, held in a cradle 170 into which the infusion medical pump 14 maybe inserted. The cradle 170 may provide a charging and storage station as well as the NFC port 110 and may have a communication line 172, for example, connecting directly to the Internet (making use of an internal Web server device) or to an auxiliary computational device such as a portable computer (not shown) in turn connected to the Internet. In this way, programming data 176 of the type described above including but not limited to drug type, delivery duration, delivery rate, and delivery volume may be loaded into the medical pump 14 according to stored delivery orders obtained from a remote source such as the medical database system 18 described above. Specifically, the mobile device 16 may receive a treatment plan (programming data 176) for controlling the portable infusion medical pump 14 over the cell phone network or other similar communication channel accessible by the mobile device 16 and then it can be relayed to the portable infusion medical pump 14 by near field communication using the NFC ports 110. In one embodiment, the NFC port 110 can be integrated to the portable infusion pump therefore eliminating the need for the cradle 170. Likewise sensed data 174 may be returned from the medical pump 14 to the medical database system 18 after it has been transferred from the portable infusion medical pump 14 to the mobile device 16 and then transmitted from the mobile device 16 using the cell phone system or other wireless communication channel accessible to the mobile device 16. The sensed data may include confirmation information establishing the proper patient identity, drug type, and pump settings, for example, as described above with respect to FIG. 8 and also log data memorializing proper delivery of the drug after pumping is complete. This data may be transmitted to multiple different sites and organizations. Status information about the infusion medical pump 14 indicating its proper operation may also be monitored by this means, for example, to trigger any necessary maintenance of the device.

It will be appreciated that the NFC port 110 of the cradle 170 may be replaced with a similar active NFC port 110 associated with a mobile device 16 described above, where the mobile device 16 may be used for programming the infusion medical pump 14 directly from its display screen 108 or to relay to a proxy device for communication of programming information 176 or sensed information 174, as described above, with a remote system using wireless or cell phone transmission protocols. In this regard, it will be appreciated that the mobile device 16 may be a separate cell phone or the like or may be a device that is incorporated into the portable infusion medical pump 14 in a socket similar to the socket 102 described above with respect to FIG. 8.

In the embodiment of FIG. 13, the portable infusion medical pump 14 may record an "odometer" value indicating its cumulative use since last service, for example, a total amount of time during which infusion activity has been conducted, or more typically, a total amount of liquid pumped by the infusion medical pump 14. These values may be reset upon service or may simply be recorded upon service and not reset to represent a lifetime odometer value for the infusion medical pump 14. Significantly, the odometer value may form a part of the sensed information 174 transmitted either directly or by means of the medical pump 14 to be reported to a remote organization responsible for service. When a service interval is exceeded, the infusion medical pump 14 may provide an alert to the patient 138 as well as transmitting this expiration information to the remote service organization. The remote service organization may contact the patient 138 when the service interval has expired as determined by reporting from the infusion medical pump 14 or by extrapolation from previous reports. During servicing of the portable infusion medical pump 14, delivery rates are checked and calibrated and other service, including inspection and replacement of wear parts, is performed.

Figure 14:
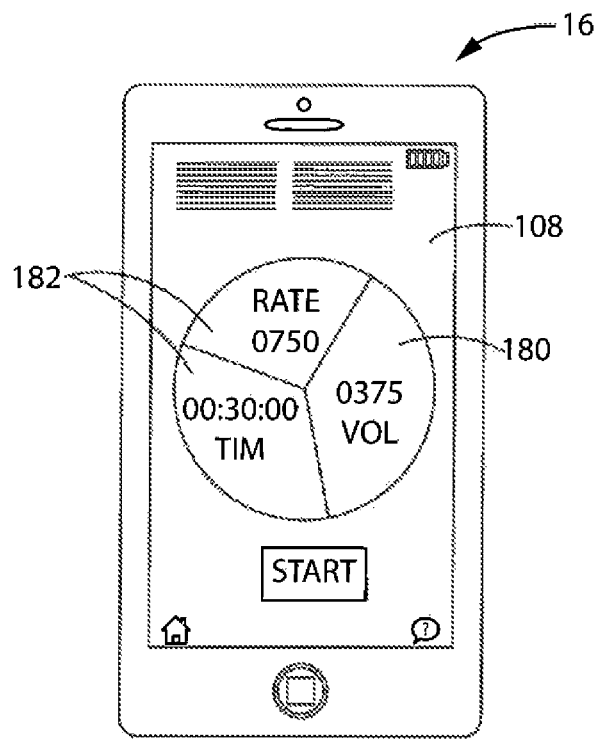
FIG. 14 is a screen display that may be provided on an infusion pump or its programming device showing the interrelationship between entered values of medicament flow rate, medicament flow time and medicament flow volume in an intuitive way.

Referring now to FIG. 14, a display screen 108 of the mobile device 16 or any display screen on the infusion medical pump 14 may provide for a graphic display 180 that intuitively shows the interrelationship between drug delivery rate, drug delivery time, and drug delivery volume, that is, how changing any one of these values necessarily causes a change in one or both of the other values. In one embodiment, this display may be in the form of a pie chart showing three sectors 182 associated one each with rate, time and volume and a quantitative display showing the setting for these particular parameters of drug delivery. The sectors 182 may be different colors and may be arranged, for example, with rate information in larger type on the upper sector emphasizing its primary importance in the setting process.

Any of the quantitative values displayed may be changed using conventional interface techniques such as a keyboard or a touchscreen-invoked menu and will change the other values of the other sectors 182 appropriately in real time to provide mathematical consistency between these values. Other confirmation information may be provided on the display screen 108 of the type described above including patient identification and drug type. The display screen. 108 may also provide for control functions such as a start button for starting the infusion medical pump 14.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

We claim:

1. A programmable medical pump comprising:
   a housing;
   a pump supported by the housing to receive an IV line and to pump medicament therethrough;
   at least one sensor supported by the housing to monitor a flow of the medicament through the IV line when received within the pump;
   a short range communication device configured to not operate wirelessly at distances greater than one meter; and
   a mobile device with a user interface including a screen and a keypad communicating through short range communication with the pump to deliver a flow rate and delivery volume of the medicament to operate the pump;
   wherein the pump further receives an indication of authorization level associated with a subset of permitted operations of the pump and accepts commands through the mobile device only if those commands are within the subset of permitted operations of the pump associated with the received indication of authorization level; and
   wherein pump commands and indication of authorization level must be received from the same, single mobile device.

2. The programmable medical pump of claim 1 wherein the mobile device communicates configuration information for controlling operation of the pump that is selected from a group consisting of operator identity, medicament identity, operating parameter data, and pump configuration data.

3. The programmable medical pump of claim 1 wherein the mobile device is selected from a group consisting of a cellular phone and a tablet computer.

4. The programmable medical pump of claim 1 wherein the mobile device receives configuration information for controlling operation of the pump from a remote electronic database through a wireless network.

5. The programmable medical pump of claim 1 wherein the short range communication device establishes a connection through optical communication between the mobile device and the pump.

6. The programmable medical pump of claim 1 wherein the short range communication device establishes a connection through electromagnetic waves between the mobile device and the pump.

7. The programmable medical pump of claim 1 wherein the short range communication device establishes a connection through radiofrequency waves between the mobile device and the pump.

8. The programmable medical pump of claim 1 further comprising:
   a wireless network communication device communicating with a remote electronic database via a wireless network; and
   an electronic computer communicating with the mobile device, the at least one sensor, the short range communication device, and the wireless network communication device and executing a stored program fixed in non-transitory media of a computer memory to:
   receive through the wireless network communication device electronically readable infusion data comprising prescribed drug data linked to patient identification data and authorization data identifying permitted operation of the pump linked to operator identification data;
   receive through the short range communication device electronically readable local drug data from a drug container proximate to the programmable medical pump;
   receive local operator identification data identifying an operator proximate to the medical pump;

receive electronically readable local patient identification data identifying a patient proximate to the medical pump;

compare the prescribed drug data with the local drug data and the linked patient identification data with the local patient identification data;

compare the authorization data linked to the operator identification data with the local operator identification data to determine a permitted operation of the pump; and permit further operation of the pump if the prescribed drug data matches the local drug data and the linked patient identification data matches the local patient identification data and if the operation is permitted.

9. The programmable medical pump of claim 8 wherein the electronic computer further executes the stored program to receive from the short range communication device, electronically readable data comprised of at least one of:

configuration information describing parameters for operating the pump;

route of administration; and pump status information indicating an operating state of the pump including but not limited to actual sensor reading, actual flow rate, alarm status, volume infused; pump setup information including but not limited to alarm threshold, sensor enable/disable status, wireless communication enable/disable status, language option, display parameters not limited to contrast and brightness, audio volume level.

10. The programmable medical pump of claim 9 wherein the electronic computer further executes the stored program to:

(a) receive from the short range communication device, data for operation of the programmable medical pump selected from the group consisting of operator identity, medicament identity, operating parameter data, and pump configuration data; and (b) operate the pump according to information received from at least one sensor and the data received from the short range communication device.

11. The programmable medical pump of claim 9 wherein the electronic computer further executes the stored program to:

(a) receive an input indicating service of the programmable medical pump indicating at least one of inspection of the pump components and repair of the pump components;

(b) monitor at least one sensor to store a reading indicating cumulative flow of material by the pump after receipt of the input indicating service of the programmable medical pump; and (c) output at least one of a reading indicating cumulative flow of material by the pump and a service indication reminder based on the cumulative flow of material.

12. The programmable medical pump of claim 8 wherein the electronically readable local patient identification data is received from a patient marker proximate to the medical pump through the short range communication device.

13. The programmable medical pump of claim 8 wherein the electronically readable infusion data further comprises an infusion protocol for drug delivery received through the wireless network communication device.

14. The programmable medical pump of claim 8 wherein the linked patient identification data includes but is not limited to a patient ID, Date of Birth, and Name.

15. The programmable medical pump of claim 8 wherein the electronic computer further executes the stored program to:

record the identity of the local operator and at least one of a time of accepting commands from the local operator and the commands accepted from the local operator.

* * * * *